US005512698A

United States Patent [19]
Casara

[11] Patent Number: 5,512,698
[45] Date of Patent: Apr. 30, 1996

[54] ETHYL 6-FORMYLOXY-4-HEXENOATE

[75] Inventor: Patrick Casara, Ittenheim, France

[73] Assignee: Merrell Pharmaceuticals Inc., Cincinnati, Ohio

[21] Appl. No.: 420,179

[22] Filed: Apr. 11, 1995

Related U.S. Application Data

[62] Division of Ser. No. 279,620, Jul. 22, 1994, Pat. No. 5,440,065, which is a division of Ser. No. 184,762, Jan. 19, 1994, Pat. No. 5,380,936, which is a continuation of Ser. No. 986,636, Dec. 7, 1992, abandoned.

[30] Foreign Application Priority Data

Dec. 10, 1991 [EP]  European Pat. Off. ........... 91403351.9

[51] Int. Cl.$^6$ ..................................................... C07C 69/73
[52] U.S. Cl. ........................................................ 560/183
[58] Field of Search ............................................. 560/183

[56] References Cited

U.S. PATENT DOCUMENTS

| Re. 31,980 | 9/1985 | Metcalf et al. . | |
|---|---|---|---|
| 3,806,540 | 4/1974 | Martel | 560/183 |
| 3,879,448 | 4/1975 | Morimoto | 560/183 |
| 3,960,927 | 6/1976 | Metcalf et al. . | |
| 4,039,549 | 8/1977 | Metcalf et al. . | |
| 4,178,463 | 12/1979 | Gittos et al. . | |
| 4,668,433 | 5/1987 | Ochsner . | |
| 4,672,140 | 6/1987 | Coleman | 560/262 |
| 4,898,977 | 2/1990 | Herold et al. . | |
| 4,912,232 | 3/1990 | Mullins et al. . | |
| 5,010,189 | 4/1991 | Herold et al. . | |
| 5,101,043 | 3/1992 | Steffen . | |

FOREIGN PATENT DOCUMENTS

| 0177807 | 4/1986 | European Pat. Off. . | |
|---|---|---|---|
| 0354201 | 2/1990 | European Pat. Off. . | |
| 0427197 | 5/1991 | European Pat. Off. . | |
| 6-92903 | 4/1994 | Japan | 560/183 |
| 22133002 | 7/1984 | United Kingdom . | |

OTHER PUBLICATIONS

Abstract—AAD89–05373, vol. 49/12–B of Dissertation Abstracts International, p. 5280; Tae Woo Kwon: "Part I. Asymmetric synthesis of 4-vinyl-4-aminobutyric acid. Part II. Section A—Thiophenyl cyclopropylcarbinyl derivatives; conversion to dithiophenylcyclobutanes. Section B—Homoallylic substitution reactions"—1988—Assignee: The University of Connecticut.

Chemical and Pharmaceutical Bulletin, vol. 26, No. 3, pp. 774–783, Pharmaceutical Society of Japan; M. Watanabe et al.: "Ubiquinone and related compounds. XXXI. Synthesis of urinary metabolites of ubiquinone, phylloquinone, alpha–tocopherol and their related compounds". Mar. 1978, Assignee: Takeda Chemical Industries.

JACS, vol. 98, No. 10, pp. 2901–2910; L. E. Overman: "A general method for the synthesis of amines by the rearrangement of allylic trichloroacetimidates. 1,5 transposition of alcohol and amine functions". May 1976—Assignee: University of California.

JACS, vol. 92, No. 3, pp. 741–743; W. S. Johnson et al.: "A simple stereo–selective version of the claisen rearrangement leading to trans–trisubstituted olefin bonds. Synthesis of squalene". Feb. 1970—Assignee: Stanford University.

Tetrahedron, vol. 44 No. 13, pp. 4243–4258 (1988)—G. Deleris et al.—"Direct regiospecific allylic amination via silicon induced pericyclic reactions. A novel synthesis of gamma vinyl gaba".

Chem. Pharm. Bull. vol. 26, No. 3, pp. 774–783 (1978)—Masazumi Watanabe et al. "Synthesis of urinary metabolites of Ubiquinone, phylloquinone, α–tocopherol and their related compounds".

J. Am. Chem. Soc. vol. 44, pp. 667–668 (1972) E. J. Corey et al. "A new method for the synthesis of macrolides".

Primary Examiner—Michael L. Shippen
Attorney, Agent, or Firm—Carolyn D. Moon

[57] ABSTRACT

This invention relates to a novel synthesis of 4-amino-5-hexenoic acid by thermal rearrangements, and to the novel intermediates produced thereby.

1 Claim, No Drawings

ETHYL 6-FORMYLOXY-4-HEXENOATE

This is a division, of application Ser. No. 08/279,620, filed Jul. 22, 1994, now U.S. Pat. No. 5,440,065, which is a division of application Ser. No. 08/184,762, filed Jan. 19, 1994, now U.S. Pat. No. 5,380,936, which is a continuation of application Ser. No. 07/986,636, filed Dec. 7, 1992, now abandoned, all of which are herein incorporated by reference.

This invention relates to a novel synthesis of 4-amino-5-hexenoic acid using thermal rearrangement reactions, and to the novel intermediates produced thereby.

4-Amino-5-hexenoic acid, otherwise known as vigabatrin or vinyl GABA is a GABA-T inhibitor marketed under the tradename SABRIL® for the treatment of epilepsy. (See *review article on vigabatrin* by S. M. Grant, et al in Drugs, 41 (6): 889–926, 1991).

In essence, this process is based upon known thermal reactions starting from erythritol; said thermal reactions being (1) an elimination process for the formation of a double bond, (2) a Claisen rearrangement and (3) an Overman rearrangement. The involved reaction sequence is depicted by the following reaction scheme.

REACTION SCHEME A

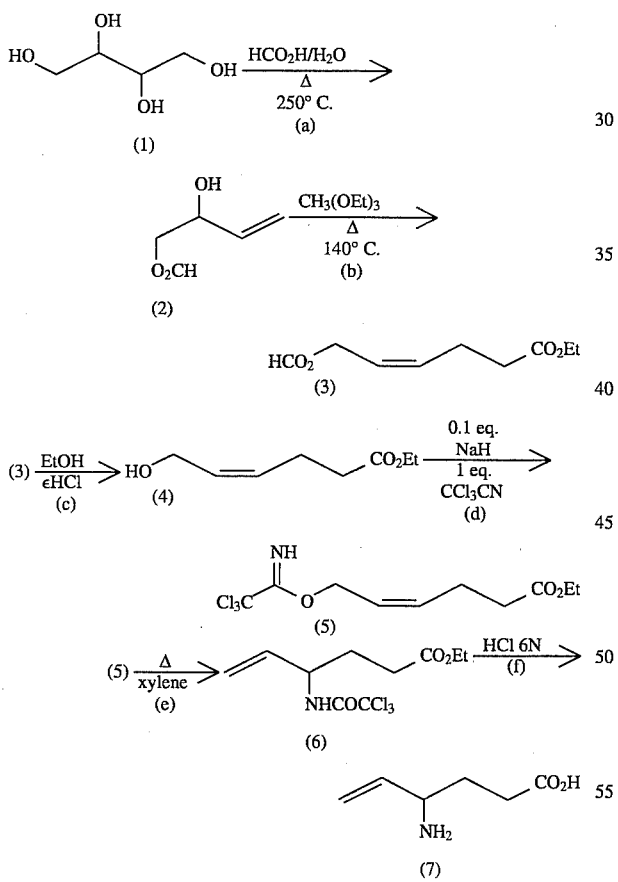

wherein Et is ethyl.

Step (a) of the process involves the known thermal rearrangement reaction for the preparation of 4-formyloxy-3-hydroxy-1-butene (2) from erythritol (1) (see Prevost, C., *Ann. Chem.* [10], 10, 398, 1928). Although no work-up is necessary, better yields of a purer compound may be obtained if the product is re-distilled. Step (b) involves a second thermal rearrangement reaction—followed by a hydrolysis—wherein 4-formyl-3-hydroxy-1-butene is heated at 140°–150° C. in the presence of excess quantities of the orthoacetate (4 to 1) under conditions for removal of the in situ produced alcohol. (See Johnson W. and Coll, *J. Am. Chem. Soc.* 92, 741, 1970). Following hydrolysis and removal of the excess orthoacetate, the so-produced product ethyl 6-formyloxy-4-hexenoate may be used as is, or it may optionally be subjected to a distillation for purification or it may be subjected to flash chromatography on $SiO_2$. Alternatively this thermal rearrangement may be effected using one equivalent of the orthoacetate in an inert solvent which boils around 140° to 150° C. (e.g. xylene). The reaction time for these reactions may be monitored by the measurement of the alcohol (methanol or ethanol) which is distilled off.

Step (c) involves the conversion of the formate to its corresponding alcohol by allowing the formate to be stirred at temperatures of about 15° to 25° C. whilst in absolute ethanol to which catalytic quantities of alcoholic HCl gas has been added. Step (d) involves the reaction of trichloroacetonitrile with ethyl 6-hydroxy-4-hexenoate in the presence of catalytic quantities of NaH ($\cong 0.1$ equivalent) in an aprotic anhydrous solvent (preferably anhydrous ether) under an inert gas, preferably nitrogen, at about 0° C. to form an in situ imidate intermediate (5) which, by thermal rearrangement, is converted to ethyl 4-trichloroacetoamido-5-hexenoate (6); the rearrangement being effected using the techniques of Overman, L. J., *Am. Chem. Soc.* 98, 2901, 1976. The final step involves the hydrolysis of the imidate, preferably by acid hydrolysis but alternatively using basic hydrolysis conditions, to produce the desired 4-amino-hexenoic acid, as its HCl salt. The free acid or other pharmaceutically acceptable salts thereof may be obtained by standard procedures well known in the art.

The advantages of this process may be summarized as follows:

(1) the process does not utilize or form carcinogenic materials, nor are any dangerous reactants or solvents utilized, (2) the starting material may be prepared from an inexpensive raw material (potato starch), (3) reaction sequence may be done with only one purification before the final hydrolysis, (4) a limited number of organic solvents are needed, (5) the excess of reactants (e.g. trichloroorthoacetate) and solvents (e.g. xylene) may be recovered and re-cyclized, (6) lack of undesirable by-products, (7) reactions are facile without problems associated with temperature control and the products may be purified without the need for chromatographic work-up.

The following example illustrates the novel process of this invention.

EXAMPLE 1

4-Amino-5-hexenoic acid

STEP A: 4-FORMYLOXY-3-HYDROXY-1-BUTENE: A solution of erythritol (50 g, 0.5 mole) in aqueous formic acid (150 g, 75%) was heated above 100° C., 12 H, then water and formic acid were distilled off and the reaction mixture was heated above 200° C. with a Bunsen burner. The product was collected by distillation (b.p. 230° C., 30 g) and should be rectified (b.p. 90° C., 15mn).

¹H NMR (90 MHz) (CDCl₃, TMS) δppm. 3.23 (s, 1 H, OH), 3.6 (m, 1 H, CH), 4.23 (t, 2 H, CH₂), 5.33 (m, 2 H, CH₂=), 5.83 (m, 1 H, —CH=), 8.16 (s, 1 H, HCO₂).

STEP B: ETHYL 6-FORMYLOXY-4-HEXENOATE: A solution of 4-formyloxy-3-hydroxy-1-butene (1.06 g, 10 mmol) and propionic acid (1 drop) in triethylorthoacetate (6 g, 40 mmol) was heated at 140° C. under conditions for distillative removal of ethanol. After 2 H, the excess of ethylorthoacetate was removed by distillation in vacuo. The residue was hydrolysed with water and extracted with AcOEt. The product was purified by flash chromatography on SiO₂ (eluant AcOEt: hexane, 2:8) (1 g, 60%) but distillative purification is preferred when larger quantities are involved.

¹H NMR (90 MHz) (CDCl₃, TMS) δppm. 1.26 (t, 3 H, CH₃, J=6 Hz), 2.4 (s, 4 H, (CH₂)₂), 4.1 (q, 2 H, CH₂, J=6 Hz), 4.6 (d, 2 H, CH₂—C=, J=6 Hz), 5.73 (m, 2 H, CH=CH), 8.06 (s, 1 H, HCO₂).

STEP C: ETHYL 6-HYDROXY-4-HEXENOATE: A solution of 6-formyloxy-6-hexenoate (0.9 g, 5 mmol) in absolute EtOH (10 mL) containing few drops of a saturated solution of alcoholic HCL gas was left 2 H at 20° C. The solvent was removed in vacuo and the residue was used for the next step without further purification (0.7 g, quantitative). This compound was found to be partially decomposed by flash chromatography on SiO₂.

¹H NMR (90 MHz) (CDCl₃, TMS) δppm. 1.26 (t, 3 H, CH₃, J=6 Hz), 2.4 (s, 4 H, (CH₂)₂), 2.83 (s, 1 H, OH), 4.1 (s, 2 H, CH₂—C=) 4.16 (q, 2 H, CH₃CH₂, J=6 Hz), 5.7 (s, 2 H, CH=CH).

STEP D: ETHYL 4-TRICHLOROACETAMIDO-5-HEXENOATE: Sodium hydride (0.03 g of a 50% dispersion in oil, 0.5 mmol, was added to a solution of ethyl 6-hydroxy-4-hexenoate (0.7 g, 5 mmol) and trichloroacetonitrile (0.6 g, 5 mmol) in anhydrous ether (50 mL) under N₂ at 0° C. After 1 H, ethanol (0.5 mmol) was added and the solvent was removed in vacuo. The formation of the imidate was controled by NMR (NH,~8.5 ppm). A solution of the crude imidate in xylene (30 mL) was heated at reflux 48 H. Then the solvent was removed in vacuo and the residue was purified by flash chromatography on SiO₂. (eluant AcOEt: hexane, 2:8) to give the title product (1.1 g, ~70%).

¹H NMR (90 MHz) (CDCl₃, TMS) δppm. 1.23 (t, 3 H, CH₃, J=6 Hz), 2.0 (t, 2 H, CH₂—CH₂—CO₂, J=5 Hz), 2.36 (s, 2 H, CH₂CO₂), 4.1 (q, 2 H, CH₃CH₂, J=6 Hz), 4.4 (t, 1 H, CH—CH₂, J=5 Hz), 5.1 (m, 2 H, CH₂), 5.76 (m, 1 H, CH=CH₂), 7.2 (s, 1 H, NH).

A sample was distilled for analysis (b.p. 150° C., 0.5 mmHg).

Analysis calculated for C₁₀H₁₄NO₃Cl₃: C: 39.69 H: 4.66 N: 4.64 Found: C: 39.87 H: 4.62 N: 4.49

STEP E: 4-AMINO-5-HEXENOIC ACID: A suspension of ethyl 4-trichloroacetoamido-5-hexenoate (0.3 g, 1 mmol) in 6N HCl (10 mL) was heated under reflux 6 H. Then the mixture was concentrated in vacuo, diluted with water (10 mL), washed twice with Acoet, and dried in vacuo to give the title product (0.18 g, 100%). NMR, TLC (NH₄OH:EtOH, 3:7) are identical with those of an authentic sample of 4-amino-5-hexenoic acid.

¹H NMR (90 MHz) (D₂O), δppm. (TMS) 1.83 (m, 2 H, CH₂CO₂), 2.33 (m, 2 H, CH₂CH₂) 3.66 (m, 1 H, CH—C=), 5.35 (m, 3 H, CH₂=CH).

What is claimed is:
1. Ethyl 6-formyloxy-4-hexenoate.

\* \* \* \* \*